United States Patent [19]

Ingle et al.

[11] 4,069,339

[45] Jan. 17, 1978

[54] NOVEL METHOD FOR THE DEPRESSION OF FAT DEPOSITION IN SWINE

[75] Inventors: Donald Lee Ingle, Trenton; Ronald Howell Dalrymple, Titusville, both of N.J.

[73] Assignee: American Cyanamid Company, Stamford, Conn.

[21] Appl. No.: 770,483

[22] Filed: Feb. 22, 1977

[51] Int. Cl.$^2$ .......................................... A61K 31/365
[52] U.S. Cl. .................................................. 424/279
[58] Field of Search ........................................ 424/279

[56] References Cited

U.S. PATENT DOCUMENTS 3,239,345  3/1966  Hodge et al. .......................... 424/279

*Primary Examiner*—Sam Rosen
*Attorney, Agent, or Firm*—Harry H. Kline

[57] ABSTRACT

There is provided a method for the depression of fat deposition in swine by administering to said swine an effective amount of the compound: 1H-2-benzoxacyclotetradecin-1-one, 3,4,5,6,7,8,9,10,11,12-decahydro-7,14,16-trihydroxy-3-methyl-, (3S), subcutaneously in the form of one or more implants.

4 Claims, No Drawings

NOVEL METHOD FOR THE DEPRESSION OF FAT DEPOSITION IN SWINE

BACKGROUND OF THE INVENTION

There is known a plurality of animal growth promoting agents represented by the following general formula:

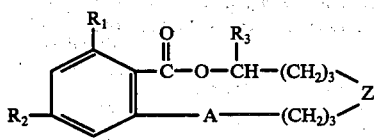

wherein $R_1$ and $R_2$ are substituents such as hydrogen, hydroxy or lower alkoxy; $R_3$ is a substituent such as hydrogen or lower alkyl; $R_4$ is a substituent such as lower alkyl, lower alkanoyl, aryl, or aralkyl; A is a bridging group such as —CH=CH— or —CH$_2$—CH$_2$—; Z is a bridging group such as >C=O, >CHOH or >CH$_2$; and when $R_3$ is lower alkyl, said compounds are the racemic mixtures and the optical isomers thereof. Among the optically active isomers the (3S) isomers are preferred, since they appear to be biologically more active than the corresponding (3R) isomers.

SUMMARY OF THE INVENTION

There is disclosed, for instance, in U.S. Pat. No. 3,239,345 the compound: zearalanol, namely: 1H-2-benzoxacyclotetradecin-1-one, 3,4,5,6,7,8,9,10,11,12-decahydro-7,14,16-trihydroxy-3-methyl-, (3S) and a method of preparation thereof, by reducing zearalenone of the formula:

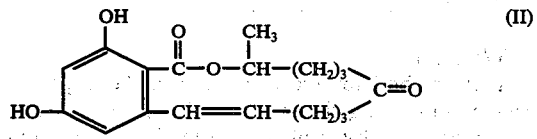

with hydrogen in the presence of Raney nickel catalyst. Although it is stated in said U.S. Patent that zearalanol is a growth promoting agent for cattle, sheep and swine, this compound has been employed exclusively in cattle and sheep, but not in swine. Further, there is no evidence that the compound exhibits any effect in lowering the deposition of fat in swine. On the contrary, there is evidence to indicate that the latter compound is useful as a growth promoting agent for ruminants especially in cattle and is virtually ineffective in preventing the deposition of fat in the ruminant animals.

Surprisingly, it has been found that zearalanol having the general formula:

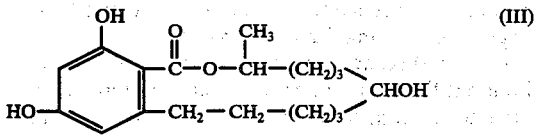

when administered to swine depresses the fat deposition in said animals.

Advantageously, an effective amount of zearalanol, namely, 1H-2-benzoxacyclotetradecin-1-one, 3,4,5,6,7,8,9,10,11,12-decahydro-7,14,16-trihydroxy-3-methyl-, or an optically active isomer thereof, is administered to swine to depress the fat deposition usually as a subcutaneous implant, or similar parenteral injection in amounts that will supply about 0.0001 mg to 0.20 mg and, preferably, from 0.005 mg to 0.10 mg per kg of body weight per day of active compound. If desired, however, the active compound can be administered in the feed, usually in amounts ranging from about 0.000001% to 0.04%, by weight, and preferably 0.00001% to 0.04% by weight of the aforementioned zearalanol to suppress the fat deposition in swine.

For a fuller understanding of the present invention, the following examples are presented. These are to be taken as illustrative and not as limitative of the invention.

EXAMPLE 1

Evaluation of Zearalanol on the Depression of Fat Deposition in Swine

A group of 30 barrows and gilts, weighing about 45 kg each, are randomly separated into three groups of 10 consisting of five barrows and five gilts each.

Each member of one group is treated with one implant, containing 12 mg of zearalanol placed subcutaneously at the base of the ear.

The second group is treated similarly, except that each animal receives five implants containing 12 mg of zearalanol each.

The third group serves as unmedicated control and each member receives an implant containing lactose, placed subcutaneously at the base of the ear.

All pigs are offered a swine finisher ration and water ad libitum. The ration consists of the following:

| Component | lbs/ton | Percent |
|---|---|---|
| Ground yellow corn | 1666 | 83.3 |
| Soybean Oil Meal (49%) | 250 | 12.5 |
| Meat and Bone Meal (50%) | 50 | 2.5 |
| Dicalcium Phosphate (18.5%P) | 15 | 0.75 |
| Iodized Salt | 10 | 0.50 |
| Limestone (38% Ca) | 7 | 0.35 |
| Mineral Premix[a] | 1 | 0.05 |
| Vitamin Premix[b] | 1 | 0.05 |
| Total: | 2000 | 100.00 |

Protein (%) = 14.7
Calcium (%) = 0.55
Phosphorus (%) = 0.53

[a]Vitamin Premix Provided per Ton

| Vitamin A | 2,000,000 I.U. |
|---|---|
| Vitamin D | 400,000 I.U. |
| Riboflavin | 4 g |
| Pantothenic acid | 10 g |
| Niacin | 20 g |
| $B_{12}$ | 10 mg |
| Menadione | 2 g |
| Vitamin E | 5,000 I.U. |

[b]Minerals Provided per Ton (ppm)

| Iron | 50 |
|---|---|
| Copper | 5 |
| Manganese | 30 |
| Zinc | 50 |

The pigs are sacrificed when they attain a live weight of 90 kg. The right side of the carcass is dissected and the subcutaneous fat and skin is separated from the lean meat and bone. The combined weight of subcutaneous fat and skin is calculated as percent of the total side weight as one indicator of carcass fat deposition.

The left side of the carcass is used to determine the carcass length, backfat thickness at the first and last rib and last lumbar vertebrae. Longissimus muscle (loin eye) cross sectional area and fat thickness over the middle of the loin eye are determined at the 10th to 11th ribs. The data obtained are averaged and summarized in Tables (I) to (V), below. The data obtained clearly show that pigs treated with five implants have decreased backfat thickness and less subcutaneous fat and skin regardless of sex.

In the single implant group the reduction in carcass fat is more pronounced in the barrows, (i.e., castrated male hogs, than in the gilts, (i.e. young sows).

Table I

Evaluation of the Effect of Zearalanol for the Depression of Backfat in the Pig, at 12 mg and 60 mg per Animal A. Backfat Thickness, in cm, Average of 3 Measurements

|  | | Zearalanol; No. of Implants | |
|---|---|---|---|
| Test Animals | Controls | 1 | 5 |
| All Pigs | 3.12 | 2.96 | 2.90 |
| Barrows | 3.20 | 2.89 | 2.85 |
| Gilts | 3.05 | 3.05 | 2.97 |

B. Backfat Thickness, % Improvement Over Controls

|  | Zearalanol; No. of Implants | |
|---|---|---|
| Test Animals | 1 | 5 |
| All Pigs | 5.1 | 7.1 |
| Barrows | 9.7 | 10.9 |
| Gilts | 0.0 | 2.6 |

Table II

Evaluation of the Effect of Zearalanol for the Depression of Loin Eye Fat Thickness in the Pig, at 12 mg and 60 mg per Animal A. Fat Thickness over Center of Loin Eye at 10–11th Rib; in cm

|  | | Zearalanol; No. of Implants | |
|---|---|---|---|
| Test Animals | Controls | 1 | 5 |
| All Pigs | 2.93 | 2.53 | 2.34 |
| Barrows | 3.14 | 2.58 | 2.44 |
| Gilts | 2.72 | 2.48 | 2.25 |

B. Fat Thickness Over Center of Loin Eye at 10–11th rib; % Improvement Over Control

|  | Zearalanol; No. of Implants | |
|---|---|---|
| Test Animals | 1 | 5 |
| All Pigs | 13.7 | 20.1 |
| Barrows | 17.8 | 22.3 |
| Gilts | 8.8 | 17.3 |

Table III

Evaluation of the Effect of Zearalanol for the Depression of Subcutaneous Ft and Skin in the Pig, at 12 mg and 60 mg per Animal A. Subcutaneous Carcass Fat and Skin Expressed as % of Total Body Weight

|  | | Zearalanol; No. of Implants | |
|---|---|---|---|
| Test Animals | Controls | 1 | 5 |
| All Pigs | 27.87 | 25.96 | 24.71 |
| Barrows | 28.81 | 25.29 | 24.35 |
| Gilts | 26.93 | 26.79 | 25.01 |

B. Subcutaneous Carcass Fat and Skin; % Improvement over Controls

|  | Zearalanol; No. of Implants | |
|---|---|---|
| Test Animals | 1 | 5 |
| All Pigs | 6.9 | 11.3 |
| Barrows | 12.2 | 15.5 |
| Gilts | 0.1 | 7.1 |

Table IV

Evaluation of the Effect of Zearalanol for Increasing the Loin Eye Area in the Pig, at 12 mg and 60 mg per Animal A. Loin Eye Area at 10–11th Ribs; in $cm^2$

|  | | Zearalanol; No. of Implants | |
|---|---|---|---|
| Test Animals | Controls | 1 | 5 |
| All Pigs | 33.68 | 33.45 | 35.01 |
| Barrows | 34.37 | 33.68 | 35.05 |
| Gilts | 32.99 | 33.16 | 34.98 |

B. Loin Eye Area at 10–11th Ribs; % Improvement Over Controls

|  | Zearalanol; No. of Implants | |
|---|---|---|
| Test Animals | 1 | 5 |
| All Pigs | — | 3.9 |
| Barrows | — | 2.0 |
| Gilts | — | 6.0 |

Table V

Evaluation of the Effect of Zearalanol on the Combined Weight of Subcutaneous Fat and Skin in the Pig, at 12 mg and 60 mg per Animal

|  |  | Weight in kg | |
|---|---|---|---|
| Treatment | Test Animal | Subcutaneous Fat + Skin | Muscle + Bone |
| Control | Barrow | 20.30 | 50.20 |
|  | Gilt | 18.30 | 49.50 |
| Zearalanol; 1 Implant/pig (12 mg/pig) | Barrow | 17.10 | 50.50 |
|  | Gilt | 18.38 | 50.24 |
| Zearalanol; 5 Implant/pig (60 mg/pig) | Barrow | 16.90 | 52.40 |
|  | Gilt | 16.84 | 50.58 |

We claim:

1. A method for the depression of fat deposition in swine comprising the step of: subcutaneously administering to swine by implant an effective amount ranging from 0.0001 mg/kg to 0.20 mg/kg of animal weight of a compound of formula:

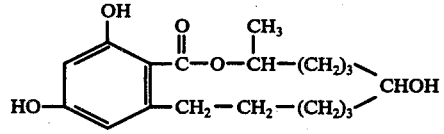

wherein said compound is the racemic mixture and the optical isomers thereof.

2. A method according to claim 1, wherein said compound is the optically active (3S) isomer.

3. A method according to claim 1, wherein said compound is administered in amounts ranging from 0.005 mg/kg to 0.10 mg/kg of animal weight.

4. A method according to claim 1, wherein said compound is the (3S) isomer, and is administered as a subcutaneous implant in amounts ranging from a total of 12 mg to 60 mg per animal.

* * * * *